United States Patent [19]

Philippbar

[11] Patent Number: 4,912,304

[45] Date of Patent: Mar. 27, 1990

[54] THICK-FILM INCUBATOR

[76] Inventor: Jay E. Philippbar, 33821 Castano Dr., Dana Point, Calif. 92629

[21] Appl. No.: 94,561

[22] Filed: Sep. 9, 1987

[51] Int. Cl.$^4$ .............................................. H05B 3/16
[52] U.S. Cl. .................................... 219/543; 219/505; 338/22 R
[58] Field of Search ............... 219/543, 504, 505, 439, 219/416, 435; 338/22 R, 306–308; 427/101; 435/290

[56] References Cited

U.S. PATENT DOCUMENTS

| | | | |
|---|---|---|---|
| 4,039,775 | 8/1977 | Andra | 219/435 X |
| 4,177,375 | 12/1979 | Meixner | 219/439 X |
| 4,298,789 | 11/1981 | Eichelberger et al. | 219/416 |
| 4,584,275 | 4/1986 | Okano et al. | 435/490 |
| 4,666,853 | 5/1987 | Meserol et al. | 435/290 |
| 4,733,056 | 3/1988 | Kojima et al. | 219/543 |

Primary Examiner—E. A. Goldberg
Assistant Examiner—M. M. Lateef
Attorney, Agent, or Firm—W. Edward Johansen

[57] ABSTRACT

A thick-film incubator is used with a temperature control circuit and a mounting member on which the thick-film incubator is disposed. The thick-film incubator includes a ceramic substrate which has a first pair of conductive pads disposed at opposite ends thereof and a second pair of conductive pads disposed opposing each other thereon. A first layer of resistive ink is deposited on the ceramic substrate so that an open rectangular field is formed. The layer has a first end and a second end which are electrically coupled to each of the first pair of conductive pads, respectively, so that current can flow through the first layer in order to heat the ceramic substrate. A second layer of temperature-dependent resistive ink is deposited on the ceramic substrate adjacent, but not contiguous, to the layer of resistive ink. The second layer has a first end and a second end which are electrically coupled to each of the second pair of conductive pads, respectively, in order to electrically couple it to the temperature control circuit. The second layer has a first side and a second side. Its first side contacts the ceramic substrate in order to sense the temperature thereof. Its second side contacts a test strip so that it can sense the temperature of the test strip in order to provide a very fast response time for precisely heating the test strip to a predetermined temperature and maintaining it at that temperature.

5 Claims, 1 Drawing Sheet

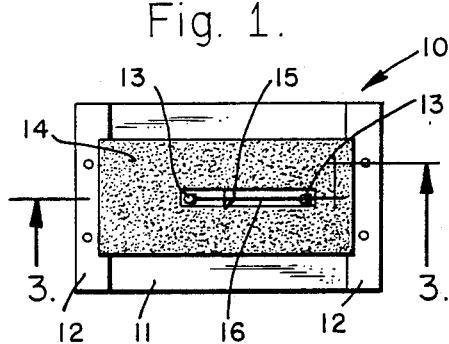
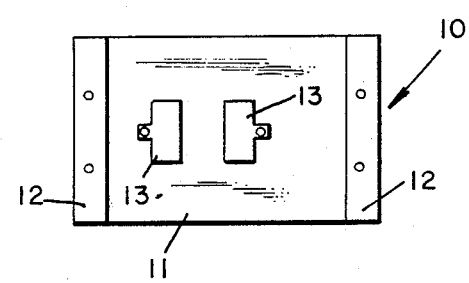
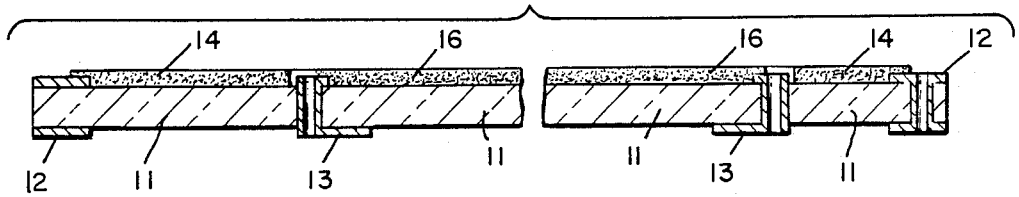
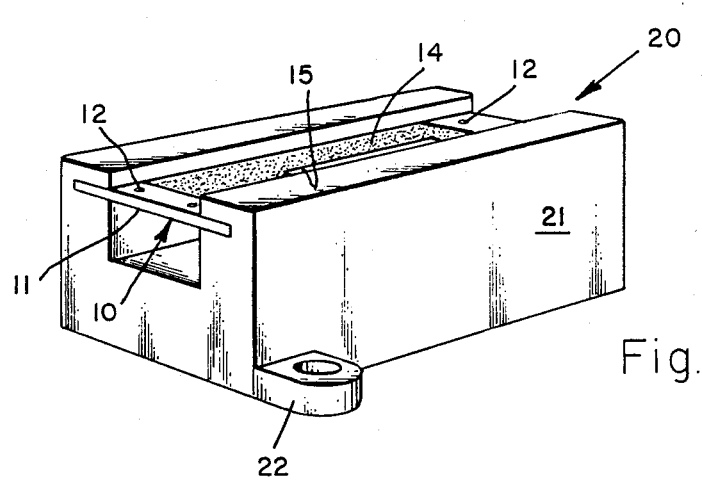
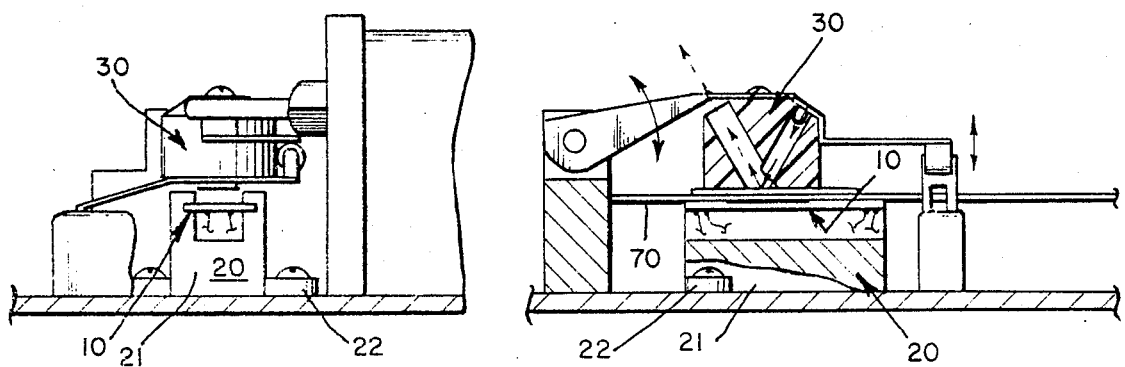

THICK-FILM INCUBATOR

BACKGROUND OF THE INVENTION

1. Field of the Invention

The present invention relates to an incubator which continuously heats a test strip to a predetermined temperature and maintains it at that temperature and which an analyzer incorporates therein for performing quantative analysis of a sample of a person's blood, serum or plasma and more particularly to a thick-film incubator which is compact and has very fast response time.

2. Description of the Prior Art

U. S. Pat. No. 4,584,275, entitled Incubator, issued to Shinichi Okano, Takashi Koizumi and Tasashi Uekusa on Apr. 22, 1986, teaches an analyzing system which includes an incubator, a light source and a photodetector. The incubator includes a heating plate, a heating element, a temperature detector and a temperature control circuit. The heating plate is made of aluminum and is maintained at a predetermined temperature according to reaction conditions. The incubator uniformly heats analysis slides to a predetermined temperature. The standard temperature for blood samples is 37° C. The heating plate has a hole adjacent to the analysis slide. A dark box is disposed below the hole and encloses the light source, a lens, a color filter and the photodetector. The light source applies light through the hole in the heating plate. In an analyzer a microprocessor may be electrically coupled to the temperature control circuit, the light source, the photodetector and a display. The microprocessor analyzes the output of the photodetector and transmits the analyzed output to the display.

U.S. Pat. No. 4,620,437, entitled Gas Sensor, issued to Yoshiaki Kuroki, Toshitaka Matsuura, Toshofumi Sekiya and Akio Takami on Nov. 4, 1986, teaches a gas sensor which includes a ceramic substrate and a heater circuit. The heater circuit has a first terminal and a second terminal at opposite ends thereof. The heater circuit is mounted on the substrate. The heater circuit has a heat-generating portion and a voltage-dividing portion connected to the second terminal. A voltage source applies a voltage through a resistive lead wire element to energize the heater circuit.

U.S. Pat. No. 4,613,455, entitled Ceramic Heater and a Method for its Production, issued to Hirofumi Suzuki, Shunzo Yamaguchi and Hitoshi Yoshida on Sept. 23, 1986, teaches a ceramic heater which includes a sintered heating element bonded to a supporting substrate.

U.S. Pat. No. 4,469,936, entitled Heating Element Suitable for Electric Space Heaters, issued to James B. Hunter on Sept. 4, 1984, teaches a heat generating element which is for use in an electrical space heater and which include an electrically nonconductive substrate on which is coated a layer of an electrically nonconductive ceramic material having finely divided, micron size metallic particles dispersed therein. Burnishing the surface of the ceramic material between two separated points establishes a conductive path in the otherwise nonconductive ceramic material. As electrical current flows along the burnished surface, the electrical resistance of the conductive path generates heat.

U.S. Pat. No. 4,464,244, entitled Oxygen Sensing Device Having Solid Electrolyte Cell and Means for Supplying Controlled Current Thereto, issued to Shigeo Isitani and Uchida Masaaki on Aug. 7, 1984, teaches a heater which includes a ceramic substrate and a heating element in operative combination therewith. A power supply applies a variable voltage to the heating element in the ceramic substrate in order to maintain the heater at a predetermined temperature by controlling the resistance of the heating element at a constant value.

U.S. Pat. No. 4,523,853, entitled Medical Test Reaction Area Reflected Light Photometric Device, issued to Klaus Nenninger and Rudolf V. Rosenbladt on June 18, 1985, teaches a reflected-light photometer which includes a light source, an integrating sphere and a photodetector. The light source diffusely illuminates the reaction area of a test strip through the integrating sphere. The photodetector directly picks up reflected light which the top chemical layer of the test strip at the reaction area diffusely reflects therefrom. Reflectance is the measure of light which the chemical layer of the test strip at the reaction area diffusely reflects therefrom. The reflected-light photometer determines reflectance of the top chemical layer of the test strip at the reaction area.

U.S. Pat. No. 4,587,099, entitled Test Strips for the Detection of a Liquid Sample Component, issued to Anselm Rothe and Bernward Sojka on May 6, 1986, teaches a test strip for analyzing a liquid sample. The test strip has a carrier, a slow-absorbent layer, a liquid impermeable layer, a reagent-absorbent layer, and a thin mesh. The slow-absorbent layer is fixed upon the carrier and slowly absorbs a sample of a person's blood, serum or plasma. The liquid impermeable layer is fixed over the slow-absorbent layer. The reagent-absorbent layer is fixed over the liquid impermeable layer and forms the top chemical layer. The thin mesh covers the carrier, the slow-absorbent layer, the liquid impermeable layer and the absorbent reagent layer. The thin mesh is fixed next to the slowly-absorbent layer onto the carrier.

SUMMARY OF THE INVENTION

In view of the foregoing factors and conditions which are characteristic of the prior art it is the primary object of the present invention to provide a thick-film incubator which continuously heats a test strip to a predetermined temperature and maintains it at that temperature.

It is another object of the present invention to provide a thick-film incubator which is compact and has very fast response time.

It is still another object of the present invention to provide an incubator which an analyzer incorporates therein for performing quantative analysis of a person's blood.

In accordance with the present invention an embodiment of a thick-film incubator for use with a temperature control circuit and a mounting member on which the thick-film incubator is disposed is described. The thick-film incubator includes a ceramic substrate which has a first pair of conductive pads disposed at opposite ends thereof and a second pair of conductive pads disposed opposing each other thereon. A first layer of resistive ink is deposited on the ceramic substrate so that an open rectangular field is formed. The first layer has a first end and a second end which are electrically coupled to each of the first pair of conductive pads, respectively, so that current flows through the first layer in order to heat the ceramic substrate. A second layer of temperature-dependent resistive ink is deposited on the ceramic substrate adjacent, but not contiguous, to the first layer. The second layer has a first end and a second end which are electrically coupled to each of the second pair of conductive pads, respectively, in order to electrically couple it to the temperature control circuit. The second layer has a first side and a second side. Its first side contacts the ceramic substrate in order to sense the temperature thereof. Its second side contacts a test strip so that it can sense the temperature of the test strip in order to provide a very fast response time for precisely heating the test strip to a predetermine temperature and maintaining it at that temperature.

The features of the present invention which are believed to be novel are set forth with particularity in the appended claims.

Other claims and many of the attendant advantages will be more readily appreciated as the same becomes better understood by reference to the following detailed description and considered in connection with the accompanying drawing in which like reference symbols designate like parts throughout the figures.

DESCRIPTION OF THE DRAWING

FIG. 1 is a top plan view of a thick-film incubator which has a layer of resistive ink on a ceramic substrate and which has been constructed in accordance with the principles of the present invention.

FIG. 2 is a bottom plan view of the thick-film incubator of FIG. 1.

FIG. 3 is a side elevational view in cross-section of the thick-film incubator of FIG. 1 along the line 3—3 of FIG. 1 with the layer of resistive ink being exaggerated in thickness in order to more clearly explain its operation.

Fig. 4 is a perspective view of an incubating assembly which includes the thick-film incubator of FIG. 1 and a mounting member.

FIG. 5 is a side elevational view in cross-section of a testing system which includes the incubating assembly of FIG. 4 and a reflected-light photometer.

FIG. 6 is a side elevational view in cross-section of the testing system of FIG. 5 wherein a test strip is in an activated position to be read.

DESCRIPTION OF THE PREFERRED EMBODIMENT

In order to best understand the present invention it is necessary to refer to the following description of its preferred embodiment in conjunction with the accompanying drawing. Referring to FIG. 1 in conjunction with FIG. 2 and FIG. 3 a thick-film incubator 10 includes a ceramic substrate 11 which has a first pair of conductive pads 12 disposed at opposite ends thereof and a second pair of conductive pads 13 disposed opposing each other thereon. A first layer 14 of resistive ink is deposited on the ceramic substrate 11 so that an open rectangular field 15 is formed. The first layer 14 has a first end and a second end which are electrically coupled to each of the first pair of conductive pads 12, respectively, in order to couple the thick-film incubator 10 to a voltage source so that the first layer 14 heats the ceramic substrate 11. A second layer 16 of temperature-dependent resistive ink is deposited on the ceramic substrate 11 adjacent, but not contiguous, to the first layer 14 within the open rectangular field 15. The second layer 16 has a first end and a second end which are electrically coupled to each of the second pair of conductive pads 13, respectively, in order to electrically couple it to a temperature control circuit. The second layer 16 has a first side and a second side. Its first side contacts the ceramic substrate 11 in order to sense the temperature thereof. Its second side contacts a test strip so that it can sense the temperature of the test strip in order to provide a very fast response time for precisely heating the test strip to a predetermined temperature and maintaining it at that temperature.

Referring to FIG. 4 in conjunction with FIG. 1 an incubating assembly 20 includes a mounting member 21 and the thick-film incubator 10. The mounting member 21 includes an attachment mechanism 22.

Referring to FIG. 5 in conjunction with FIG. 4 and FIG. 6 an application, entitled Precise Reflected-Light Photometer, filed by Norman S. Hughes on Sept. 9, 1987, teaches a precise reflected-light photometer 30 which includes a light source and a photodetector and which is for use with test strip having a top chemical layer and a plastic cover. The precise reflected-light photometer includes a light source and a photodetector. The light source is disposed in a first plane which is orthogonal to the top chemical layer. The light source illuminates with direct light the top chemical layer. The direct light is in the first plane. The top chemical layer diffusely reflects the direct light into all of the planes which are orthogonal to the top chemical layer. Reflectance is the diffuse reflection which is the result of scattering within the top chemical layer. Diffusely reflected light does not have a direction of preference and is uniformly distributed. The photodetector is disposed in a second plane which is also orthogonal to the top chemical layer. The second plane intersects the first plane. The photodetector only picks up light which the top chemical layer directly reflects into the second plane so that the photodetector ignores most of the undesirable light which either the surface of the plastic cover directly reflects or flaws on the surface of the plastic cover diffusely reflects in order to increase the precision in measuring light which the top chemical layer diffusely reflects.

From the foregoing it can be seen that a thick-film incubator for use with a temperature control circuit and a mounting member on which the thick-film incubator is disposed has been described. It should be noted that the sketches are not drawn to scale and that distance of and between the figures are not to be considered significant.

Accordingly it is intended that the foregoing disclosure and showing made in the drawing shall be considered only as an illustration of the principles of the present invention.

What is claimed is

1. A thick-film incubator for use with a temperature control circuit, said thick-film incubator comprising:
   a. a ceramic substrate having a first electrically conductive pad and a second electrically conductive pad disposed at opposite ends thereof and also having a third electrically conductive pad and a fourth electrically conductive pad disposed opposing each other thereon;
   b. heating means for heating said ceramic substrate, said heating means being disposed on said ceramic substrate and being electrically coupled to said first and second electrically conductive pad; and
   c. temperature sensing means for sensing the temperature of said ceramic substrate, said temperature sensing means being disposed on said ceramic substrate with said temperature sensing means and being electrically coupled to the temperature control circuit, said temperature sensing means having a first side and a second side with its said first side being disposed on said ceramic substrate.

2. A thick-film incubator for use with a temperature control circuit according to claim 1 wherein said heating means comprises a first layer of resistive ink which is deposited on said ceramic substrate so that an open rectangular field is formed and which has a first end and second which are electrically coupled to said first and second conductive pads, respectively.

3. A thick-film incubator for use with a temperature control circuit according to claim 2 wherein said temperature sensing means comprises a second layer of temperature-dependent resistive ink which is deposited on said ceramic substrate adjacent, but not contiguous, to said first layer within said open rectangular field and which has a first end and a second end which are electrically coupled to said third and fourth conductive pad, respectively.

4. A thick-film incubator for use with a temperature control circuit according to claim 1 wherein said temperature sensing means comprises a second layer of temperature-dependent resistive ink which is deposited on said ceramic substrate adjacent, but not contiguous, to said heating means and which has a first end and a second end which are electrically coupled to said third and fourth conductive pad, respectively.

5. An incubating assembly including a thick-film incubator for use with a temperature control circuit and a mounting member for said thick-film incubator, said thick-film incubator comprising:
   a. a ceramic substrate which has a first electrically conductive pad and a second electrically conductive pad at opposite ends thereof and also has a third electrically conductive pad and a fourth electrically conductive pad disposed opposing each other thereon, said ceramic substrate being disposed on the mounting member;
   b. heating means for heating said ceramic substrate, said heating means being disposed on said ceramic substrate and being electrically coupled to said first and second electrically conductive pad; and
   c. temperature sensing means for sensing the temperature of said ceramic substrate, said temperature sensing means being disposed on said ceramic substrate with said temperature sensing means and being electrically coupled to the temperature control circuit, said temperature sensing means having a first side and a second side with its said first side being disposed on said ceramic substrate.

* * * * *